United States Patent [19]

Collington et al.

[11] 4,438,112
[45] Mar. 20, 1984

[54] PROSTANOID COMPOUNDS AND PHARMACEUTICAL FORMULATIONS

[75] Inventors: Eric W. Collington, Welwyn; Peter Hallett, Buntingford; Christopher J. Wallis, Royston; John Bradshaw, Ware, all of England

[73] Assignee: Glaxo Group Limited, London, England

[21] Appl. No.: 419,521

[22] Filed: Sep. 17, 1982

Related U.S. Application Data

[63] Continuation of Ser. No. 223,315, Jan. 8, 1981, abandoned.

[30] Foreign Application Priority Data

Jan. 9, 1980 [GB] United Kingdom ................. 8000697

[51] Int. Cl.[3] .................... A61K 31/53; A61K 31/54; C07D 295/14
[52] U.S. Cl. .................................. 424/244; 544/171; 424/246; 544/357; 544/360; 424/248.51; 544/366; 544/372; 424/248.53; 544/379; 544/399; 424/248.54; 544/400; 546/187; 424/248.55; 546/188; 546/190; 424/250; 546/208; 546/210; 424/267; 546/213; 546/221; 424/274; 546/233; 546/234; 424/275; 546/232; 546/235; 424/269; 546/238; 546/239; 424/45; 542/426; 548/253; 544/58.1; 548/527; 548/567; 544/58.2; 548/569; 548/573; 544/58.5; 260/243.3; 260/244.4; 544/58.6; 260/245.5; 544/58.7; 260/239 BF; 544/82; 260/330.3; 260/330.6; 544/85; 544/86; 544/87; 544/107; 544/109; 544/110; 544/121; 544/130; 544/132; 544/141; 544/146; 544/158; 544/159; 544/165; 544/167

[58] Field of Search ................... 544/58.1, 58.2, 58.5, 544/58.6, 58.7, 82, 85, 86, 87, 109, 110, 107, 121, 146, 158, 171, 357, 360, 399, 400, 130, 132, 141, 159, 165, 167, 366, 372, 379; 546/187, 188, 190, 233, 234, 235, 239, 221, 208, 210, 213, 232, 238; 548/253, 527, 567, 569, 573; 542/426; 260/243.3, 244.4, 330.3, 330.6, 245.5, 239 BF; 424/244, 246, 248.53, 248.54, 250, 267, 269, 45, 248.51, 248.55, 274, 275

[56] References Cited

U.S. PATENT DOCUMENTS

| | | | |
|---|---|---|---|
| 4,182,903 | 1/1980 | Favara et al. | 562/503 |
| 4,189,606 | 2/1980 | Favara et al. | 562/455 |
| 4,239,778 | 12/1980 | Venton et al. | 424/305 |
| 4,265,891 | 5/1981 | Collington et al. | 424/244 |
| 4,327,092 | 4/1982 | Collington et al. | 424/246 |
| 4,342,756 | 8/1982 | Collington et al. | 424/244 |
| 4,371,530 | 2/1983 | Collington et al. | 424/244 |

Primary Examiner—Robert W. Ramsuer
Attorney, Agent, or Firm—Bernard, Rothwell & Brown

[57] ABSTRACT

Prostanoids are described of the formulae

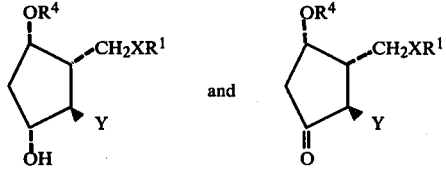

(and the salts thereof) in which:
X is cis or trans —CH=CH— or $CH_2CH_2$—;
$R^1$ is $C_{1-7}$ alkyl terminated by —$COOR^{10}$ where $R^{10}$ is H, $C_{1-6}$ alkyl or aralkyl;
Y is a saturated heterocyclic amino group; and
$R^4$ is aralkyl (in which the aryl portion is substituted by alkylthio, alkylsulphinyl, alkylsulphonyl, alkanoylamino, aroylamino, phenalkyl, aminosulphonyl, alkanoylaminosulphonyl, phenylsulphonyl, nitro, tetrazolyl, substituted phenyl or thienyl).

These compounds inhibit blood platelet aggregation and have bronchodilatory action, and may be formulated for use as anti-asthmatics and antithrombotic agents.

8 Claims, No Drawings

PROSTANOID COMPOUNDS AND PHARMACEUTICAL FORMULATIONS

This is a continuation of application Ser. No. 223,315 filed Jan. 8, 1981 now abandoned.

Prostaglandins are a class of naturally occurring cyclopentane derivatives which are biologically active in many physiological systems and they and substances which antagonise their effects are therefore of considerable interest in both human and veterinary medicine.

In view of the activity found in the natural prostaglandins, considerable effort has been directed towards the preparation of synthetic analogues. Many such compounds have been described, and in general it has been reported that these compounds possess activity within the same spectrum as the natural compounds. The synthetic compounds can however have increased selectivity of action, longer duration of activity or different potency, and in some cases they can antagonise the activity of natural prostaglandins.

In most of the synthetic prostanoids previously reported, the side chains have been attached to the cyclopentane ring via carbon atoms, as in the natural prostaglandin structure. We have now found a new class of prostanoid compounds in which the α-side chain has the same or similar structure to that of the natural compounds, while the β-side chain is attached to the ring via a nitrogen atom and the ring is also substituted by certain aralkoxy groups. Compounds in this class have shown prostanoid activity in our tests and in particular they inhibit blood platelet aggregation and have bronchodilatatory action.

The invention provides prostanoids of the general formula (1)

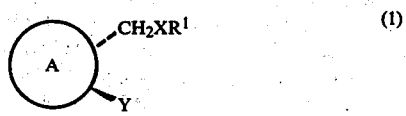

(1)

in which
A represents

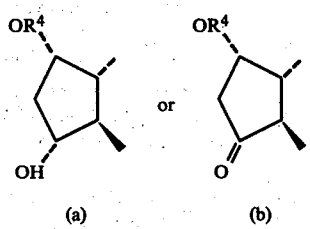

X is cis or trans —CH=CH— or —(CH$_2$)$_2$—;
R$^1$ is straight or branched C$_{1-7}$ alkyl bearing as a terminal substituent —COOR$^{10}$ where R$^{10}$ is a hydrogen atom, C$_{1-6}$ alkyl or C$_{7-10}$ aralkyl (e.g. benzyl);
Y represents (i) —NR$^2$R$^3$ where R$^2$ and R$^3$ are the same or different and are each a hydrogen atom, aralkyl having a C$_{1-7}$ alkyl portion or C$_{1-10}$ alkyl, both alkyls being optionally substituted by one or more substituents —OR$^7$ (where R$^7$ is a hydrogen atom, C$_{1-7}$ alkyl, aryl or aralkyl having a C$_{1-4}$ alkyl portion) or —NR$^8$R$^9$ (where R$^8$ and R$^9$ are the same or different and are each a hydrogen atom or C$_{1-4}$ alkyl, or where —NR$^8$R$^9$ is a saturated heterocyclic amino group (as defined below for Y; any aryl group in R$^2$ or R$^3$ being optionally substituted by one or more C$_{1-4}$ alkyl or trifluoromethyl groups; always provided that the total number of carbon atoms in the group —NR$^2$R$^3$ does not exceed 15;
or (ii) a saturated heterocyclic amino group which has 5-8 ring members and (a) optionally contains in the ring —O—, —S—, —SO$_2$, —NR$^{14}$— (where R$^{14}$ is a hydrogen atom, C$_{1-7}$ alkyl or aralkyl having a C$_{1-4}$ alkyl portion), >C(OH)R$^6$ (where R$^6$ is a hydrogen atom, C$_{1-7}$ alkyl, phenyl, or aralkyl having a C$_{1-4}$ alkyl portion); and/or (b) is optionally substituted by one or more C$_{1-4}$ alkyl groups;
R$^4$ is aralkyl (having a C$_{1-3}$ alkyl portion and the aryl portion being substituted by C$_{1-3}$ alkylthio, C$_{1-3}$ alkylsulphinyl, C$_{1-3}$ alkylsulphonyl, C$_{1-3}$ alkanoylamino, aroylamino (e.g. benzoylamino), phenylalkyl having a C$_{1-3}$ alkyl portion, aminosulphonyl, (the amino group being optionally substituted by one or two C$_{1-3}$ alkyl groups), C$_{1-3}$ alkanoylaminosulphonyl (the amino group being optionally substituted by C$_{1-3}$ alkyl), phenylsulphonyl (the phenyl portion being optionally substituted by C$_{1-3}$ alkyl) nitro, tetrazol-5-yl, phenyl substituted by R$^5$ (where R$^5$ is C$_{1-4}$ alkyl, C$_{1-4}$ alkoxy, halogen or phenyl), or thienyl);
and the physiologically acceptable salts thereof.

The formulae used herein are to be understood to depict either or both optical isomers of each of the compounds concerned as well as mixtures of the isomers, including racemates, even though the precise structure as set out only relates to one optical isomer.

Compounds having the ring type (b) are particularly important.

In the group —CH$_2$XR$^1$, the alkyl portion of the group R$^1$ may for example contain 2-5 carbon atoms (straight or branched) and is preferably —(CH$_2$)$_3$COOR$^{10}$. R$^{10}$ is preferably a hydrogen atom or C$_{1-4}$ alkyl, e.g. methyl, particularly hydrogen.

When R$^1$ is terminally substituted by —COOH, the compounds are capable of salt formation with bases, examples of suitable salts being alkali metal (e.g. sodium and potassium), alkaline earth metal (e.g. calcium), ammonium, substituted ammonium (e.g. tromethamine or dimethylaminoethanol), piperazine, morpholine, piperidine and tertiary amine (e.g. triethylamine) salts. X is preferably —CH$_2$CH$_2$— or cis —CH=CH—, particularly the latter.

In the group Y, when one of R$^2$ and R$^3$ is alkyl or substituted alkyl, the alkyl group preferably contains no more than 7 (e.g. 2-7) carbon atoms and preferably has a straight chain. Examples of such groups are n-hexyl and n-heptyl. In such compounds, the other group of R$^2$ or R$^3$ is preferably hydrogen or methyl. When R$^2$ or R$^3$ is an aralkyl group, it may for example be benzyl, phenethyl or phenpentyl.

In the optional substituent —OR$^7$ on R$^2$ or R$^3$, examples of R$^7$ are a hydrogen atom, methyl, n-butyl, phenyl, benzyl and phenethyl. The optional amino substituent —NR$^8$R$^9$ may for example be —NH$_2$, —NHMe, —NHEt, —NMe$_2$ or —NEt$_2$. These optional substituents may for example be carried at the β-position, as in β-hydroxyalkyl groups. Two —OR$^7$ groups may be present, particularly on an R$^2$ or R$^3$ alkyl group; for example, there may be a hydroxy group at the β-position and a second —OR$^7$ group at the terminal position.

Aryl (e.g. phenyl) groups in R$^2$ and R$^3$ may themselves be substituted, e.g. by C$_{1-4}$ alkyl or trifluoromethyl.

Compounds in which Y is a saturated heterocyclic amino group are however preferred. The types of heterocyclic group which are generally preferred are those in which the ring has 5–8 members and (a) optionally contains —O—, —S—, —SO$_2$— or —NR$^{14}$— and/or (b) is optionally substituted by one or more C$_{1-4}$ alkyl (e.g. methyl) groups. The group may for example have a 5, 6 or 7-membered ring, e.g. pyrrolidino, piperidino, morpholino, piperazino, thiamorpholino, 1-dioxothiamorpholino, homomorpholino and hexamethyleneimino.

Examples of the optional substituents which may be present on a second nitrogen atom in the ring are methyl, ethyl and benzyl. The carbon atoms of the heterocyclic rings may for example be substituted by methyl or ethyl. The group C(OH)R$^6$ may for example be present in a piperidino ring and when R$^6$ is other than hydrogen it may for example be methyl, ethyl or butyl.

Compounds in which Y is a morpholino, dioxothiamorpholino or piperidino group are particularly preferred.

The amino group in the group Y enables the compounds to form salts with inorganic or organic acids, e.g. hydrochlorides, sulphates, acetates, maleates and succinates.

R$^4$ is preferably an arylmethyl (particularly benzyl) group substituted by C$_{1-3}$ alkylthio (e.g. methylthio), C$_{1-3}$ alkylsulphinyl (e.g. methylsulphinyl), C$_{1-3}$ alkanoylamino (e.g. acetylamino), C$_{1-3}$ alkylsulphonyl (e.g. methylsulphonyl), arylsulphonyl (e.g. phenylsulphonyl), aminosulphonyl (e.g. dimethylaminosulphonyl), phenylalkyl (e.g. phenethyl or benzyl), phenyl substituted by the group R$^5$ (where R$^5$ represents C$_{1-4}$ alkyl (e.g. methyl), C$_{1-4}$ alkoxy (e.g. methoxy), halogen (e.g. chlorine), or phenyl), or thienyl. Particularly preferred substituents of this type are phenylalkyl (e.g. phenethyl or benzyl), or, more particularly, phenyl substituted by C$_{1-3}$ alkoxy (e.g. methoxy) or C$_{1-3}$ alkyl (e.g. methyl).

A particularly preferred group of compounds has the formula 1(b) where:
X is cis —CH=CH—,
R$^1$ is —(CH$_2$)$_3$COOH,
Y is morpholino, piperidino, or 1-dioxothiamorpholino, and
R$^4$ is benzyl substituted by phenethyl, benzyl, methoxyphenyl or methylphenyl.

As indicated above, our tests have shown that compounds of formula (1) inhibit blood platelet aggregation and/or have bronchodilatatory activity. The test we have used for bronchodilatation is as described by K. M. Lulich, et al in British Journal of Pharmacology 58, 71–79, (1976) except guinea-pig lung is used instead of cat lung. The test for inhibition of platelet aggregation is as described by G. V. Born in Nature 194, 927–929 (1962) except collagen is used instead of ADP as the pro-aggregatory agent.

The compounds are thus of interest in the treatment of asthma and as antithrombotic agents for use in the treatment and prevention of cardiovascular diseases or conditions such as arteriosclerosis, atherosclerosis and myocardial infarcts. They may be formulated for use in conventional manner, with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by bolus injections or continuous infusion. Formulations for injections may be presented in unit dosage form in ampoules, or in multi-dose containers, with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use as antithrombotic agents, the compounds are preferably administered orally, for example in amounts of 0.1 to 10 mg/kg body weight, 1 to 4 times daily. For use in the treatment of asthma, the compounds may also be administered orally in amounts of 0.1 to 10 mg/kg body weight, 1 to 4 times daily; preferably however they are administered by inhalation in the form of aerosols or solutions for nebulisers, at doses varying from 0.3 to 30 mg, 1 to 4 times daily. The compounds may be used in combination with other anti-asthmatic agents. It will be appreciated that the precise dose administered will always depend on the age and condition of the patient.

The compounds of formula (1) may be prepared by selection and adaptation of methods known in prostanoid chemistry (see for example British Patent Specification 2028805A). Method (a) below is particularly important in forming certain prostanoids of the desired class, and other compounds in the class can be prepared from them by known techniques for example using one or more of methods (b) to (m) below.

The following reactions will frequently require the use of (or will conveniently be applied to) starting materials having protected functional groups (e.g. hydroxy). It is to be understood that references to the use of starting materials of a particular structure are intended to include starting materials having protected functional groups. Certain of the reactions described below are capable of affecting other groups in the starting material which are desired in the end product, and this must be taken into account when performing multi-stage reactions.

In the discussion below, the groups X and Y and the various R groups are as defined above except where otherwise indicated.

(a) Compounds of formula (2)

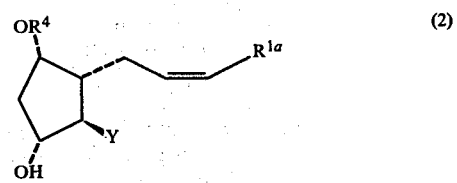

(where R$^{1a}$ is as defined above for R$^1$ where R$^{10}$ is a hydrogen atom) may be prepared by reacting lactols of formula (3) or their aldehyde isomers of formula (3a)

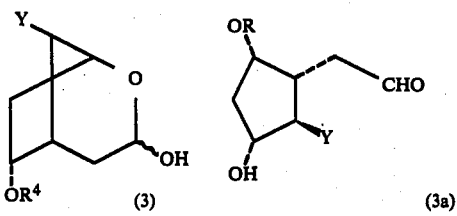

with appropriate Wittig reagents, e.g. a phosphorane of formula $R_3^{12}P=CHR^{1a}$ (where $R^{12}$ is $C_{1-6}$ alkyl or aryl, e.g. monocyclic aryl such as phenyl), or a salt thereof, e.g. the potassium salt. Suitable reaction solvents include hydrocarbons (e.g. benzene and toluene), ethers (e.g. tetrahydrofuran), dialkylsulphoxides (e.g. dimethylsulphoxide), alcohols and halogenated hydrocarbons. The reaction may be carried out at any suitable temperature up to 50° C., preferably at room temperature.

The reaction is particularly suitable for the preparation of compounds in which $R^1$ is terminally substituted by —COOH (in salt form). Any hydroxy group in Y should preferably be in a protected state prior to this reaction. Suitable hydroxy protecting groups are described below. Any —NH₂ group present should also be protected, e.g. by t-butoxycarbonyl.

Except as regards the nature of $R^4$, this reaction is the same as process (a) of British Patent Specification 2028805A. The intermediates of formulae (3) and (3a) may thus be prepared by the methods described in that specification, using starting materials containing the desired $R^4$ group.

These starting materials may themselves be prepared by the same general methods as described in Specification 2028805A. However, when $R^4$ is an aralkyl group substituted by phenylmethyl, substituted phenyl or thienyl, it can be more convenient to introduce first an aralkyl $R^4$ group substituted by halo; after the formation of the intermediate lactone, this group can then be modified to form the desired $R^4$ group, for example by treatment with the appropriate aryl or benzyl zinc halide in the presence of a catalyst such as $Ni(PPH_3)_4$ or $Cl_2Pd(PPh_3)_2$/diisobutylaluminium hydride in a solvent such as tetrahydrofuran at e.g. 10°-ambient temperature.

(b) Compounds of ring type (b) may be prepared by oxidising the corresponding hydroxy compound of ring type (a), for example with a $Cr^{VI}$ oxidising reagent, e.g. Jones reagent, at −10° to room temperature, preferably −10°-0°, in a solvent such as acetone. Other conventional methods can also be used, for example using dimethylsulphoxide and a suitable electrophilic reagent, such as acetyl bromide, oxalyl chloride, thionyl chloride, or dicyclohexylcarbodiimide in a hydrocarbon solvent such as toluene at low temperature e.g. −70°. With the latter reagent, the reaction is preferably carried out in the presence of trifluoroacetic acid or its pyridinium salt.

Other suitable reagents are N-chlorosuccinimidedimethylsulphide complex (used for example in a hydrocarbon solvent, such as toluene, e.g. at 0°-5°), and pyridine-sulphur trioxide complex in dimethylsulphoxide (e.g. at 0° to room temperature).

When the α-side chain has a terminal —COOH group (i.e. when $R^{10}$ is hydrogen), better yields are sometimes obtained by prior protecting the carboxyl group, for example in the form of a trialkyl (e.g. trimethyl or triethyl) silyl ester.

Any other hydroxy group present should be protected in this reaction.

(c) Compounds in which $R^{10}$ is alkyl or aralkyl can be prepared by esterification of the corresponding carboxylic acid (in which $R^{10}$ is hydrogen). Conventional esterification techniques may be used, reaction with a diazoalkane being preferred. The alkyl esters may also be formed by reaction with an appropriate alcohol in the presence of a mineral acid, e.g. hydrochloric or sulphuric acid.

(d) Compounds in which $R^1$ is terminally substituted by a —COOH group can be prepared by saponifying a corresponding ester, e.g. using KOH or NaOH in methanol.

(e) Compounds in which X is trans —CH=CH— may be prepared by isomerising the corresponding cis compound. The isomerisation may be effected by treatment with, for example, p-toluene sulphinic acid in dioxan (e.g. at reflux) or azobisisobutyronitrile and thiophenol, using for example a hydrocarbon solvent and any suitable temperature up to reflux. Where an oxo group is desired in the end product, it should be introduced after this reaction.

(f) Compounds in which X is —(CH₂)₂— may be prepared by catalytic hydrogenation of a corresponding compound in which X is —CH=CH—. Conventional catalysts may be used, preferably palladium or platinum on carbon, in a suitable solvent (e.g. an alcohol such as methanol) e.g. at room temperature.

(g) Compounds of formula (1a) may be prepared by etherification of the corresponding hydroxy compound (in which $R^4$ represents hydrogen), for example by reaction with an appropriate halide ($R^4$ Hal), for example by reaction at room temperature in the presence of a suitable base (e.g. sodium sodium hydride) in a suitable solvent (e.g. dimethylformamide).

Any other hydroxy group present in the starting material (e.g. the ring hydroxy group) should be protected in this reaction.

Starting materials for this reaction may be prepared by the same general technique as described above for process (a), using intermediates in which the group —OR⁴ is a protected hydroxy group and removing the protecting group prior to etherification.

Starting materials of the formula (4)

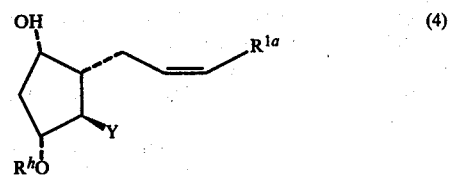

(where $R^{1a}$ is as defined above and —OR^h represents a protected hydroxy group) may also be prepared by method (b) of British Patent Specification 2028805A.

(h) Compounds having ring type (a) can be prepared by removing the protecting group from the corresponding compound in which the ring hydroxy group is protected, for example by reduction or acid or alkaline hydrolysis. This is discussed below in connection with hydroxy group protection.

(i) Compounds in which $R^4$ is aralkyl substituted by alkanoylamino may be prepared by acylation of the corresponding amine, e.g. with the appropriate acid anhydride in an organic base such as pyridine at 0° C.

(j) Compounds of formula (1a) in which $R^4$ is aralkyl substituted by alkylsulphinyl or alkylsulphonyl may be prepared by oxidation of the corresponding alkylthio compound with a peracid for example peracetic acid at room temperature.

(k) Compounds of formula (1a) in which Y is a substituted amino group may be prepared by substitution of the corresponding compound in which Y is —$NH_2$.

This reaction may be performed by treating the starting material with a compound of the formula $JR^{13}J$, where J is a readily displaceable group (such as halo, e.g. iodo, or hydrocarbylsulphonyloxy, e.g. p-toluenesulphonyloxy) and $R^{13}$ is the appropriate divalent group (e.g. —$(CH_2)_2O(CH_2)_2$—). The reaction may be carried out in a solvent such as acetonitrile or methanol, in the presence of a suitable base, e.g. potassium carbonate or sodium bicarbonate.

Alternatively, the starting material may be reacted with an appropriate dialdehyde or diketone in the presence of a reducing agent. For example, reaction with glutardialdehyde gives a compound in which Y is piperidino. The reducing agents which may be used are those generally known for the reduction of imines, e.g. formic acid, or an alkali metal borohydride or cyanoborohydride (e.g. sodium borohydride or potassium cyanoborohydride, using an alcohol such as ethanol as solvent, suitably at room termperature, preferably at pH 4–6), or hydrogen in the presence of a metal catalyst, e.g. palladium.

The amines required as starting materials may be prepared by reduction of the corresponding azide, for example as described for process (1).

(1) Compounds of ring type (a) in which Y is —$NH_2$ and $R^{10}$ is hydrogen may be prepared by reducing the corresponding compound in which Y represents an azido group.

Compounds in which X is —$(CH_2)_2$— may thus be prepared by catalytic hydrogenation, using for example platinum or palladium on carbon as the catalyst. However, when compounds in which X is —CH=CH— are required, selective reduction methods specific for the azide function should be used. Examples of suitable reagents are zinc and sodium dihydrogen phosphate in a suitable solvent (e.g. tetrahydrofuran); zinc and methanol/sulphuric acid; or triphenyl phosphine followed by methanol/sulphuric acid.

The azido starting materials required for this reaction may be prepared by methods analogous to those for preparing the compounds of formula (2), using reagents in which Y is azido. These methods are analogous to those of process (c) of British Patent Specification No. 2028805A.

(m) Salts of the compounds of formula (1) may be prepared by conventional methods, e.g. by treatment with an acid or (where $R^{10}$ is hydrogen) a base in a suitable solvent e.g. water or an organic solvent such as ether.

In the preparation of compounds of formula (1) the ring hydroxy group (or any other hydroxy group present) will often be protected and its liberation will frequently be the last step in the preparation. Conventional methods of protection may be used, protection in the form of t-butyldimethylsilyloxy or tetrahydropyranyloxy groups being preferred. These groups may be removed by acid hydrolysis. The group may also be protected in the form of an alkanoyloxy group having up to 7 carbon atoms, e.g. acetoxy. Such groups may be removed by alkaline hydrolysis.

The examples below illustrate the invention. The preparation of the intermediates required is described first.

The preparation of the following intermediates is described in British Patent Specification 2028805 A:

Intermediate 4:
(±)-3-endo-Hydroxy-2-exo-(4-morpholinyl)bicyclo[3.2.0]heptan-6-one Intermediate 5:
(3aα,4α,5β,6aα)-(±)-Hexahydro-5-hydroxy-4-(4-morpholinyl)-2H-cyclopenta(b)furan-2-one Intermediate 6:
(3aα,4α,5β,6aα)-(±)-Hexahydro-4-(4-morpholinyl)-5-(tetrahydro-2H-pyran-2-yl)oxy-2H-cyclopenta(b)furan-2-one Intermediate 7:
(3aα,4α,5β,6aα)-(±)-Hexahydro-4-(4-morpholinyl)-5-(tetrahydro-2H-pyran-2-yl)oxy-2H-cyclopenta(b)furan-2-ol Intermediate 8:
[1α(Z),2β,3α,5α]-(±)-Methyl 7-[5-Acetoxy-2-(4-morpholinyl)-3-[(tetrahydro-2H-pyran-2-yl)oxy]cyclopentyl]-5-heptenoate Intermediate 9:
[1α(Z),2β,3α,5α]-Methyl 7-[5-Hydroxy-2-(4-morpholinyl)-3-[(tetrahydro-2H-pyran-2-yl)oxy]cyclopentyl]-5-heptenoate Intermediate 10:
[1α(Z),2β,3α,5α]-(±)-Methyl 7-[5-[4-Amino(phenylmethoxy)]-3-hydroxy-2-(4-morpholinyl)cyclopentyl]-5-heptenoate Intermediate 11:
(±)-6-endo-(Phenylmethoxy)-8-anti-(4-thiomorpholinyl)-2-oxabicyclo[3.2.1]octan-3-one Intermediate 41:
[1α(Z),2β,3α,5α]-(±)-Methyl 7-[5-Hydroxy-2-(1-piperidinyl)-3-[(tetrahydro-2H-pyran-2-yl)oxy]cyclopentyl]-5-heptenoate Temperatures are in °C. The following abbreviations are used:

TLC—thin layer chromatography, PE—petroleum ether (boiling at 40°–60° unless otherwise stated), THF—tetrahydrofuran, EA—ethyl acetate, PTSA—p-toluenesulphonic acid monohydrate, DMF—dimethylformamide, DMSO—dimethylsulphoxide, Dibal—diisobutylaluminium hydride.

Chromatography was carried out using silica gel. TLC was carried out using $SiO_2$. The following abbreviations illustrate the eluent used for the chromatography and TLC:

(A) 9:1 PE (b.p. 60°–80°)—EA; (B) 4:1 PE (b.p. 60°–80°)—EA; (C) 3:1 PE-ether; (D) ether-EA; (E) 9:1 EA-PE; (F) ether-PE; (G) 4:1 ether-PE; (H) 7:3 ether-PE; (I) 9:1 ether-methanol; (J) ether; (K) EA; (L) 19:1 ether-methanol; (M) 1:1 ether-PE (b.p. 60°–80°); (N) 9:1 EA-PE (b.p. 60°–80°); (O) EA-PE (b.p. 60°–80°); (P) 19:1 EA-methanol; (Q) 95:5 ether-methanol; (R) 85:15 EA-methanol; (S) 3:1 EA-methanol; (T) 98:2 chloroform-methanol; (U) 95:5 EA-methanol; (V) 4:1 ether-methanol; (V) PE; (X) 9:1 EA-methanol; (Y) 7:3 EA-PE; (Z) 3:2 ether-PE; (AB) 1:1 EA-PE; (AC) 4:1 ether-isopentane; (AD) 39:1 ether-methanol; (AE) 4:1 ether-PE (b.p. 60°–80°); (AF) ether-isopentane; (AG) chloroform; (AH) 97:3 chloroform-methanol; (AI) 7:3 EA-PE (b.p. 60°–80°); (AJ) 85:15 ether-methanol; (AK) 97:3 ether-methanol; AL 99:1 ether-methanol; (AM) ether-methanol.

Intermediate 1

1-(Bromomethyl)-4-(2-phenylethyl)benzene

A solution of methyl 4-(2-phenethenyl)benzoate (5.4 g) in EA (200 ml) was hydrogenated over pe-reduced 10% Pd on charcoal (1 g) at atmospheric pressure. When hydrogen uptake had ceased the mixture was filtered and evaporated to give a solid (5.4 g).

A solution of the solid (4.7 g) in dry THF (20 ml) was added dropwise to a stirred suspension of LiAlH$_4$ (0.59 g) in dry THF (20 ml) at 0°. After 1 h Rochelle salt solution (50 ml) was added and the mixture extracted with EA (3×50 ml), washed with brine and dried (MgSO$_4$). PBr$_3$ (0.81 ml) was added to a solution of the dried extracts (3.4 g) in dry ether (75 ml) at 0° and the mixture was stirred for 0.5 h. Ice-water (70 ml) was added and stirring continued for a further 0.5 h. The aqueous phase was separated and extracted with ether (2×70 ml), washed with NaHCO$_3$ solution, brine and then dried (MgSO$_4$). Evaporation in vacuo gave the title compound as a solid (3.8 g) which was purified from PE (bp 60°-80°) to give material of m.p. 52°-3°.

Intermediate 2

[4'Methyl-(1,1-biphenyl)-4-yl]methanol

4-Methyl-(1,1'-biphenyl)-4-carboxylic acid, methyl ester (1.43 g) in ether (25 ml) and THF (25 ml) was added over 5 min to LiAlH$_4$ (420 mg) in ether (25 ml). The mixture was stirred at room temperature for 1 h and then cooled in ice. Aqueous NaOH (1 M, 2.1 ml) was added and after stirring (15 min) excess anhydrous Na$_2$SO$_4$ was added. The mixture was filtered and the filtrate evaporated to give a solid. Crystallisation from cyclohexane-methanol gave the title compound (1.04 g) m.p. 128°-31°.

Intermediate 3

4-Bromomethyl-4'-methyl (1,1'-biphenyl)

To a cold (0°) solution of Intermediate 2 (0.917 g) in dry CH$_2$Cl$_2$ (14 ml) was added PBr$_3$ (0.29 ml). After stirring for 1 h at 0°, 8% NaHCO$_3$ solution (30 ml) was added and the layers separated. The aqueous layer was extracted with CH$_2$Cl$_2$ (2×30 ml), dried (MgSO$_4$) and evaporated to give a solid (0.99 g). Crystallisation from PE (b.p. 60°-80°) afforded the title compound (0.91 g) m.p. 100°-102°.

Intermediate 12

(±)-7-anti-(4-Morpholinyl)-5-endo-[tetrahydro-2H-pyran-2-yl)oxy]bicyclo[2.2.1]heptan-2-one Morpholine (76 ml) was added dropwise over 15 mins to a stirred solution of 2-exo-bromo-3-endo-[(tetrahydro-2H-pyran-2-yl)oxy]bicyclo[3.2.0]heptan-6-one (100.8 g) in acetone (500 ml) at 0°. After 2 h at 5° the mixture was stirred at 20° for 18 h and then filtered. Evaporation of the filtrate gave an oil which was taken into ether (350 ml), filtered and washed (water, 2×100 ml). The ethereal solution was dried (MgSO$_4$), filtered and evaporated to give the title compound as a solid. Purification from PE gave material (85.5 g) of m.p. 86°-88°.

Intermediate 13

(a) 1-Bromomethyl-4-phenylsulphonyl benzene

A solution of p-tolyl phenylsulphone (20 g) in refluxing CCl$_4$ (400 ml) containing dibenzoyl peroxide (0.4 g) was treated with N-bromosuccinimide (15.3 g) in portions rapidly. The mixture was heated under reflux for 30 min., filtered whilst hot and the filtrate allowed to cool. Evaporation gave the title compound (26.8 g), m.p. (103°-104°.

(b) N,N-Dimethyl, 4-bromomethylbenzenesulphonamide, m.p. 94°-96° was prepared by a similar procedure from N,N-dimethyl-p-toluenesulphonamide.

Intermediate 25

(±)-5-endo-Hydroxy-7-anti-(4-morpholinyl)bicyclo[2.2.1]heptan-2-one, hydrochloride To a stirred solution of Intermediate 12 (96.4 g) in methanol (600 ml) was added an ethereal solution of HCl (240 ml) and the mixture stirred at 20° for 2.5 h (pH 1.5-2). Filtration followed by evaporation of the filtrate gave an oil which solidified on trituration with EA (2×200 ml). Coloured impurities were removed by extraction with boiling isopropanol to leave the title compound as a solid (70.6 g), m.p. 181°-182°.

Intermediate 26

(a) (±)-5-endo-(4-Bromophenylmethoxy)-7-anti-(4-morpholinyl)bicyclo[2.2.1]heptan-2-one Aqueous NaOH solution (10 N; 200 ml) was added to a solution of the free base of Intermediate 25 (21.1 g), benzyltriethylammonium chloride (4 g) and 4-bromobenzyl bromide (27.5 g) in CH$_2$Cl$_2$ (400 ml) and the mixture stirred vigorously for 4 h. A further portion of 4-bromobenzylbromide (9 g) was then added and stirring continued for 68 h. Water (200 ml) was added and the layers separated. The aqueous layer was extracted with EA (2×75 ml), washed with water, dried (MgSO$_4$) and evaporated to give an oil (48 g) which solidified on standing. Excess alkylating agent was removed by trituration with PE (b.p. 60°-80°) and crystallisation from EA-PE (b.p. 60°-80°) then gave the title compound (34.1 g) as a solid, m.p. 130°-131°.

The following compounds were prepared by a similar procedure:

(b) (±)-7-anti-(4-Morpholinyl)-5-endo[4-phenylsulphonyl(phenylmethoxy)]bicyclo[2.2.1]heptan-2-one, m.p. 133°-135°, from Intermediates 25 and 13a). Purification by chromatography twice (D), then (E)

Intermediate 27

(±)-8-anti-(4-Morpholinyl)-6-endo-[4-phenylsulphonyl(phenylmethoxy)cyclopentyl]-2-oxabicyclo[3.2.1]octan-3-one To a stirred solution of Intermediate 26b) (2.12 g) in CH$_2$Cl$_2$ (22 ml) at 0° was added peracetic acid (3.14 ml, 6.12 M) and the resulting solution then stirred at ambient temperature for 18 h. Excess Na$_2$SO$_3$ solution was added to the cooled solution and stirring continued for 1 h. After evaporation in vacuo the residue was suspended in NaHCO$_3$ solution (50 ml), extracted with EA (3×70 ml), dried (MgSO$_4$), filtered and concentrated to give the title compound as a solid (1.16 g), m.p. 170°-171° (from EA-acetone-PE).

Intermediate 28

(a) (±)-6-endo-(4-Bromophenylmethoxy)-8-anti-(4-morpholinyl)-2-oxabicyclo[3.2.1]octan-3-one Intermediate 26(a) (13.2 g) in acetic acid (110 ml) and water (55 ml) containing CH$_3$COONa.3H$_2$O (23.7 g) was cooled (ca. 5°-10°) and stirred during the dropwise addition of peracetic acid (6.1 M; 28.5 ml). The resulting solution was stirred at 20° for 48 h when 10% Na$_2$SO$_3$ solution (200 ml), was added, maintaining the temperature of the mixture at 10°-15°. After 1.5 h solvents were removed in vacuo at 35°, the residue taken into water (150 ml) and basified to pH 9 with Na$_2$CO$_3$ solution. Extraction with EA (3×200 ml) followed by drying and evaporation gave a solid which crystallised from EA to give the title compound (5.49 g), m.p. 154°-156°.

Intermediate 29

(±)-8-anti-(4-Morpholinyl)-6-endo-[[[4-(phenylmethyl)phenyl]-4-yl]methoxy]-2-oxabicyclo[3.2.1]octan-3-one To a stirred suspension of activated Zn dust (13.08 g) in THF (40 ml) was added dropwise over 0.5 h a solution of benzyl bromide (11.9 ml) in THF (40 ml), the internal temperature being maintained at 10°. The mixture was then stirred at 10°–15° for 1 h. Nickel acetylacetonate (0.774 g) and triphenylphosphine (3.14 g) were dissolved in THF (15 ml) and stirred at 20° under nitrogen during the dropwise addition of Dibal (1 M in hexane, 3 ml). After 5 min. a solution of Intermediate 28a) (2.77 g) in THF (35 ml) was added, followed after a further 5 min. by the solution of benzylzinc bromide described above. The mixture was stirred at 29° for 19 h and then poured into NH$_4$Cl solution (250 ml) and EA (150 ml). 2 N hydrochloric acid was added to pH 6 and the layers were separated. The aqueous solution was extracted with EA (100 ml), dried and concentrated. Purification by chromatography (K). Crystallisation from EA-PE gave the title compound (2.3 g), m.p. 119°–121°.

Intermediate 30

(a) (±)-6-endo-[[4'-Methoxy(1,1'-phenyl)-4-yl]methoxy]-8-anti-(4-morpholinyl)-2-oxabicyclo[3.2.1]octan-3-one 4-Bromoanisole (7.48 g) in ether (30 ml) was added to Mg turnings (1.06 g) in THF (40 ml) containing a small iodine crystal. After 0.5 h an exothermic reaction took place which was moderated by water bath cooling. The resultant mixture was stirred at 20° for a further 0.5 h and then added, under nitrogen, to a stirred, cooled (5°) solution of anhydrous ZnBr$_2$ (9.0 g) in THF (40 ml) and stirred for 1 h.

Dibal (1 M in hexane; 5.72 ml) was added dropwise to a suspension of bis(triphenylphosphine)palladium chloride (2.0 g) in THF (20 ml). After stirring for 5 min. a solution of Intermediate 28(a) (2.38 g) in THF (35 ml) was added followed after a further 5 min. by the solution of 4-methoxyphenylzinc bromide described above. The resultant mixture was stirred under nitrogen at 20° for 18 h. The solvent was then removed in vacuo, NH$_4$Cl solution (150 ml) added and the mixture extracted with EA (3×100 ml). Evaporation of the dried extracts gave an oil which was chromatographed (K) to give the title compound as a solid. Crystallisation from EA-PE (b.p. 60°–80°) gave material (1.58 g) of m.p. 123°–125°.

(b) (±)-8-anti-(4-Morpholinyl)-6-endo-[[(1,1':4,1''-terphenyl)-4-yl]methoxy]-2-oxabicyclo[3.2.1]octan-3-one, m.p. 196°–198° was similarly prepared from Intermediate 28(a) and biphenylzinc chloride.

(c) (±)-6-endo-[4-(Thien-2-yl)phenylmethoxy]-8-anti-(4-morpholinyl)-2-oxabicyclo[3.2.1]octan-3-one, m.p. 216°–217° was similarly prepared from Intermediate 28(a) and a solution of anhydrous ZnBr$_2$ and the Grignard reagent from 2-bromothiophene and Mg in dry THF. Purification by chromatography, EA-PE (b.p. 60°–80°) (1:2, 1:1 and 2:1 successively).

Intermediate 31

(3aα,4α,5β,6aα)-(±)-Hexahydro5-hydroxy-4-(4-thiomorpholinyl)-2H-cyclopenta(b)furan-2-one, S-dioxide, hydrochloride A solution of the product of Preparation 30 (British Patent Specification 2028805A) (10 g) in ethanol (60 ml) and water (40 ml) containing concentrated hydrochloric acid (40 ml) was hydrogenated over prereduced 10% palladium oxide on charcoal (5 g, 50% dispersion in water) in ethanol (40 ml). The mixture was filtered and the filtrate evaporated in vacuo to give the title compound as a solid (8.55 g), m.p. above 230° (dec.) (from water-ethanol).

Intermediate 32

(3aα,4α,5β,6aα)-(±)-Hexahydro-5-[(tetrahydro-2H-pyran-2-yl)oxy]-4-(4-thiomorpholinyl)-2H-cyclopenta(b)furan-2-one, S-dioxide Dihydropyran (3.1 ml) was added to a stirred solution of the free base of Intermediate 31 (1.56 g) and PTSA (1.17 g) in dry DMF (30 ml) at −10°. The mixture was allowed to reach ambient temperature and stirring continued for 18 h, whereupon it was poured into saturated aqueous NaHCO$_3$ solution (50 ml), extracted with EA (4×100 ml), washed with water, dried (MgSO$_4$), filtered and concentrated. The residue was chromatographed (L) to give the title compound as a viscous oil (1.89 g). IR (CHBr$_3$) 1762 cm$^{-1}$.

Intermediate 33

(a) (1α,2β,3α,5α)-(±)-3-Hydroxy-5-[[4'-methoxy(1,1'-biphenyl)-4-yl]methoxy]-2-(4-morpholinyl)cyclopentane acetaldehyde A solution of Intermediate 30(a) (1.6 g) in CH$_2$Cl$_2$ (25 ml) at −70° under dry nitrogen was stirred during the addition of Dibal (1 M in hexane, 8.7 ml). After 1.5 h at −70°, methanol (25 ml) was carefully added and the mixture was then allowed to rise to ambient temperature whereupon stirring was continued for 18 h. The mixture was filtered through 'Hyflo' and the filtrate evaporated to give the title compound as a foam (1.68 g). IR(CHBr$_3$) 3580/3560 (br), 1715, 1240, 1040 cm$^{-1}$.

The following compounds were prepared by a similar procedure:

(b) (1α,2β,3α,5α)-(±)-3-Hydroxy-2-(4-morpholinyl)-5-[[(1,1':4,1''-terphenyl)-4-yl]methoxy]cyclopentane acetaldehyde, m.p. 154°–156° C. from Intermediate 30(b).

(c) (1α,2β,3α,5α)-(±)-3-Hydroxy-2-(4-morpholinyl)-5-[[4-(phenylmethyl)phenyl]methoxy]cyclopentane acetaldehyde, from Intermediate 29, IR (CHBr$_3$) 3590, 1715 cm$^{-1}$.

(d) (1α,2β,3α,5α)-(±)-3-Hydroxy-2-(4-morpholinyl)-5-[4-(thien-2-yl)phenylmethoxy]cyclopentane acetaldehyde, from Intermediate 30c), TLC (U) Rf 0.3.

(e) (1α,2β,3α,5α-(±)-3-Hydroxy-2-(4-morpholinyl)-5-[4-phenylsulphonyl(phenylmethoxy)]cyclopentane acetaldehyde, from Intermediate 27, IR (CHBr$_3$) 1705 cm$^{-1}$.

(f) (3aα,4α,5β,6aα)-(±)-Hexahydro-5-[(tetrahydro-2H-pyran-2-yl)oxy]-4-(4-thiomorpholinyl)-2H-cyclopenta(b)furan-2-ol, S-dioxide, from Intermediate 32

Analysis Found: C, 53.2; H, 7.6; N, 3.5. C$_{16}$H$_{27}$NO$_6$S requires: C, 53.2; H, 7.5; N, 3.9%.

Intermediate 35

[1α(Z),2β,3α,5α]-(±)-Methyl 7-[3-Acetoxy-5-[4-acetylamino(phenylmethoxy)]-2-(4-morpholinyl)cyclopentyl]-5-heptenoate Intermediate 10 (0.7 g) in acetic anhydride (10 ml) and pyridine (15 ml) was stood at room temperature for 18 h. After evaporation in vacuo the residue was treated with 8% aqueous NaHCO$_3$ solution (50 ml), extracted with ether (3×30 ml), dried (MgSO$_4$), filtered and concentrated to give the title compound as an oil (0.62 g). IR (CHBr$_3$) 3430, 1730, 1690, 1510 cm$^{-1}$.

Intermediate 37

[1α(Z),2β,3α,5α]-(±)-Methyl 7-[5-Hydroxy-3-[(tetrahydro-2H-pyran-2-yl)oxy]-2-(4-thiomorpholinyl)cyclopentyl]-5-heptenoate, S-oxide To a stirred solution of potassium t-butoxide (1.12 g) in dry THF (10 ml) under dry nitrogen was added (4- carboxybutyl)triphenylphosphonium bromide (2.21 g) and the mixture stirred at 22° for 15 min., whereupon a solution of Intermediate 33(f) (0.9 g) in THF (5 ml) was added and stirring continued for a further 30 min. Water (50 ml) was added and the mixture extracted with EA (3×25 ml). The aqueous phase was adjusted to pH 6.5 with $KH_2PO_4$ solution and then extracted with EA (3×30 ml), washed with brine, dried ($MgSO_4$) and treated with ethereal diazomethane. Concentration gave an oil which was chromatographed (L) to give the title compound (0.63 g).

Analysis Found: C, 57.8; H, 8.3; N, 2.9. $C_{22}H_{37}NO_7S$ requires: C, 57.5; H, 8.1; N, 3.1%.

Intermediate 38

[1α(Z),2β,3α,5α]-(±)-Methyl 7-[3-Acetoxy-5-[4-N,N-dimethylaminosulphonyl(phenylmethoxy)]-2-(4-morpholinyl)cyclopentyl]-5-heptenoate Intermediates 9 (2.5 g) and 13b (5.08 g) were converted into the hydroxy analogue of the title compound by the method of Example 1. The residue was treated with acetic anhydride (0.9 ml) in dry pyridine (10 ml) at room temperature for 18 h. The mixture was diluted with ether, washed with $NaHCO_3$ solution and brine, dried ($MgSO_4$) and concentrated. Purification of the residue by chromatography (J) gave the title compound as an oil (0.8 g). IR (Neat) 1730, 1340, 1160 cm$^{-1}$.

Intermediate 39

4-Bromomethyl-4'-chloro-1,1'-biphenyl

4'-Chloro(1,1'-biphenyl)-4-methanol (5.8 g) was converted into the title compound (6.8 g), m.p. 64°-66° by the method for the preparation of Intermediate 3.

Intermediate 40

[1α(Z),2β,3α,5α]-(±)-Methyl 7-[5-[[4'-Chloro(1,1'-biphenyl)-4-yl]methoxy]-2-(4-morpholinyl)-3-[(tetrahydro-2H-pyran-2-yl)oxy]cyclopentyl]-5-heptenoate To a stirred solution of Intermediate 9 (2.6 g) and NaH (75% dispersion in oil, 0.6 g) in dry DMF (20 ml) was added after 5 min. a solution of Intermediate 39 (5.3 g) in DMF (10 ml). The mixture was stirred for 5 h at room temperature, then poured into $NH_4Cl$ solution and extracted with ether. The dried ($MgSO_4$) extracts were evaporated and the residue chromatographed eluting successively with (1:4; 1:2; 1:1; 2:1) EA-PE (b.p. 60°-80°) and 4:1 EA-methanol to give the title compound as an oil (1.8 g). IR (Neat) 1732, 1090 cm$^{-1}$.

EXAMPLE 1

(a) [1α(Z),2β,3α,5α]-(±)-Methyl 7-[5-[[4'-methyl(1,1'-biphenyl)-4-yl]methoxy]-3-hydroxy-2-(4-morpholinyl)cyclopentyl]-5-heptenoate A solution of Intermediates 9 (0.43 g) and 3 (0.68 g) in dry DMF (6 ml) was stirred at 0° under nitrogen during the addition of NaH (0.08 g, 80% dispersion in oil). After 4 h at 20°, the mixture was carefully poured into saturated aqueous $NH_4Cl$ (70 ml) and extracted with ether (3×40 ml). The combined extracts were dried ($MgSO_4$), filtered and evaporated, and the residue then stirred with 5% methanolic sulphuric acid (20 ml) at 20° for 2 h. The mixture was poured into 8% $NaHCO_3$ solution (100 ml), extracted with ether (3×50 ml), dried ($MgSO_4$), evaporated and the residue purified by chromatography (P). The title compound was crystallised from ether-PE as needles (0.14 g), m.p. 75°-77°.

The following compounds were prepared by a similar procedure:

(b) [1α(Z),2β,3α,5α](±)-Methyl 7-[3-Hydroxy-5-[4-methylthio(phenylmethoxy)]-2-(4-morpholinyl)cyclopentyl]-5-heptenoate from Intermediate 11 and 1-(bromomethyl)-4-(methylthio)benzene Analysis Found: C,65.1; H 8.0; N, 2.9; $C_{25}H_{37}NO_5S$. requires: C,64.8; H, 8.0; N, 3.0%.

(c) [1α(Z),2β,3α,5α]-(±)-Methyl 7-[3-Hydroxy-2-(4-morpholinyl)-5-[4-(2-phenylethyl)phenylmethoxy]cyclopentyl]-5-heptenate, from Intermediates 9 and 1, IR (Neat) 3460, 1740 cm$^{-1}$. Purification by chromatography (Q)

(d) [1α(Z),2β,3α,5α]-(±)-Methyl 7-[3-Hydroxy-5-[[4'-meth-oxy(1,1'biphenyl)-4-yl]methoxy]-2-(1-piperidinyl)cyclopentyl]-5-heptenoate, IR (Neat) 1735 cm$^{-1}$, from Intermediate 41 and 4-bromomethyl-4'-methoxy(1,1'-biphenyl). Purification by chromatography (R).

(e) [1α(Z),2β,3α,5α]-(±)-Methyl 7-[3-Hydroxy-5-[4-(phenylmethyl)phenylmethoxy]-2-(1-piperidinyl)cyclopentyl]-5-heptenoate, IR (Neat) 3440, 1735 cm$^{-1}$, from Intermediate 41 and 1-bromomethyl-4-(phenylmethyl)benzene. Purification by chromatography (R).

(f) [1α(Z),2β,3α,5α]-(±)-Methyl 7-[3-Hydroxy-5-[[4'-methyl(1,1'-biphenyl)-4-yl]methoxy]-2-(1-piperidinyl)cyclopentyl]-5-heptenoate, from Intermediate 41 and Intermediate 3, purification by chromatography (S). IR (CHBr$_3$) 3600/3500, 1722 cm$^{-1}$. TLC (S) R$_f$ 0.28

(g) [1α(Z),2β,3α,5α]-(±)-Methyl 7-[3-Hydroxy-5-[[4'-methoxy(1,1'-biphenyl)-4-yl]methoxy]-2-(4-thiomorpholinyl)cyclopentyl]-5-heptenoate, S-dioxide from Intermediate 37 and 4-bromomethyl-4'-methoxy(1,1'-biphenyl). Purification by chromatography (L). IR (CHBr$_3$) 3580/3500, 1723 cm$^{-1}$. TLC (I) R$_f$ 0.36.

(h) [1α(Z),2β,3α,5α]-(±)-Methyl 7-[3-Hydroxy-5-[4-(phenylmethyl)phenylmethoxy]-2-(4-thiomorpholinyl)cyclopentyl]-5-heptenoate, S-dioxide, from Intermediate 37 (1 g) and 1-bromomethyl-4-(phenylmethyl)benzene (1.76 g). Purification by chromatography (J) increasing to (Q). IR (CHBr$_3$) 3580-3480 (br.), 1730 cm$^{-1}$. TLC (Q) R$_f$ 0.42.

(i) [1α(Z),2β,3α,5α]-(±)-Methyl 7-[3-Hydroxy-5-[[4'-methyl(1,1'-biphenyl)-4-yl]methoxy]-2-(4-thiomorpholinyl)cyclopentyl]-5-heptenoate, S-dioxide, from Intermediates 37 and 3. Purification by chromatography (L). IR (Neat) 3520 (br.), 1740, 1302, 1123 cm$^{-1}$. TLC (I). R$_f$ 0.61.

EXAMPLE 2

(a) [1α(Z),2β,3α,5α]-(±)-7-[3-Hydroxy-5-[[4'-methyl(1,1'-biphenyl)-4-yl]methoxy]-2-(4-morpholinyl)cyclopentyl]-5-heptenoic acid A suspension of the product of Example 1(a) (0.44 g) in methanol (2 ml) and water (4 ml) containing KOH (0.35 g) was stirred at room temperature for 7 h. The methanol was removed and the residue further diluted with water (75 ml), washed with ether (75 ml) and then carefully acidified to pH 6 with 2 N hydrochloric acid. Extraction with ether (4×50 ml) followed by drying and evaporation gave the title compound (0.35 g) as a foam. IR (CHBr$_3$) 3500, 3200(br.), 1730, 1700 cm$^{-1}$. TLC (X) R$_f$ 025.

The following compounds were prepared by a similar procedure:

(b) [1α(Z),2β,3α,5α]-(±)-7-[3-Hydroxy-5-[4-methylthio(phenylmethoxy)]-2-(4-morpholinyl)cyclopentyl]-5-heptenoic acid from the product of Example 1(b). Purification by chromatography (I).

Analysis Found: C, 63.5; H, 8.1; N, 3.0; $C_{24}H_{35}NO_5S$. Requires: C, 64.1; H, 7.9; N, 3.1%.

(c) [1α(Z),2β,3α,5α]-(±)-7-[3-Hydroxy-2-(4-morpholinyl)-5-[4-(2-phenylethyl)phenylmethoxy]cyclopentyl]-5-heptenoic acid, IR (Neat) 3350, 1700 cm$^{-1}$, from the product of Example 1(c).

EXAMPLE 3

(a) [1α,(Z),2β,3α,5α]-(±)-Methyl 7-[3-Hydroxy-5-[4-methylsulphonyl(phenylmethoxy)]-2-(4-morpholinyl)-cyclopentyl]-5-heptenoate Peracetic acid (6.12 M, 0.49 ml) in acetic acid (10 ml) was added dropwise to a mixture of the product of Example 1(b) (0.7 g) and CH$_3$COONa (0.25 g) in acetic acid (15 ml) at 0°. After stirring for 2 h saturated Na$_2$SO$_3$ solution was added and the suspension evaporated to dryness. The residue was neutralised with 8% NaHCO$_3$ solution, extracted with CH$_2$Cl$_2$ (3×75 ml), dried (MgSO$_4$), filtered and evaporated to afford an oil (0.83 g). Column chromatography (V) gave the title compound as an oil (0.4 g). TLC (V) R$_f$ 0.36.

(b) [1α(Z),2β,3α,5α]-(±)-Methyl 7-[3-Hydroxy-5-[4-methylsulphinyl(phenylmethoxy)]-2-(4-morpholinyl)-cyclopentyl]-5-heptenoate was prepared from the product of Example 1(b) (0.7 g) according to the method of Example 3(a). Continued elution of the column using (V) gave the title compound as an oil (0.13 g). IR (CHBr$_3$) 3580/3440, 1723, 1040 cm$^{-1}$. TLC (V) Rf 0.2.

EXAMPLE 4

(a) [1α(Z),2β,3α,5α]-(±)-7-[3-Hydroxy-5-[[4'-methoxy(1,1'-biphenyl)-4-yl]methoxy]-2-(4-morpholinyl)cyclopentyl]-5-heptenoic acid, hydrochloride To a solution of potassium t-butoxide (2.28 g) in THF (15 ml) under dry nitrogen was added (4-carboxybutyl)-triphenylphosphonium bromide (4.5 g). After 15 min at 20° a solution of Intermediate 33 (1.6 g) in THF was added and stirring continued for a further 1 h. Water (2 ml) was added and the THF removed in vacuo. The residue was taken up into water (100 ml), basified (pH 10) with NaOH solution and washed with ether (2×75 ml). The aqueous layer was adjusted to pH 6 with 2 N hydrochloric acid, extracted with ether (5×75 ml), dried, evaporated and re-dissolved in EA (25 ml) and ether (40 ml). To the solution was added an excess of ethereal hydrogen chloride solution followed by cooling until crystallisation occurred. Filtration and purification from EA-methanol gave the title compound (1.2 g) m.p. 164°-166°.

The following compounds were prepared by a similar procedure:

(b) [1α(Z),2β,3α,5α]-(±)-7-[3-Hydroxy-2-(4-morpholinyl)-5-[4-(phenylmethyl)phenylmethoxy]cyclopentyl]-5-heptenoic acid, hydrochloride, m.p. 167°-169° from Intermediate 33(c).

(c) [1α(Z),2β,3α,5α]-(±)-7-[3-Hydroxy-2-(4-morpholinyl)-5-[[(1,1';4',1''-terphenyl)-4-yl]methoxy]cyclopentyl-5-heptenoic acid, hydrochloride, m.p. 188°-190° from Intermediate 33(b).

(d) [1α(Z),2β,3α,5α]-(±)-7-[3-Hydroxy-2-(4-morpholinyl)-5-[4-phenylsulphonyl(phenylmethoxy)]cyclopentyl]-5-heptenoic acid, from Intermediate 33(e). Purification by chromatography (Q). (IR (CHBr$_3$), 1730(sh), 1705 cm$^{-1}$, TLC (V) R$_f$ 0.27.

(e) [1α(Z),2β,3α,5α]-(±)-7-[3-Hydroxy-2-(4-morpholinyl)-5-[4-thien-2-yl)phenylmethoxy]cyclopentyl]-5-heptenoic acid, from Intermediate 33(d). Purification by chromatography (W) followed by (X). IR (Neat 3360, 1710 cm$^{-1}$, TLC (X) R$_f$ 0.4.

EXAMPLE 5

(a) [1α(Z),2β,5α]-(±)-7-[5-[[4'-Methyl(1,1'-biphenyl)-4-yl]methoxy]-2-(4-morpholinyl)-3-oxocyclopentyl]-5-heptenoic acid To a stirred solution of the product of Example 2 (0.393 g) in DMSO (2 ml) and CH$_2$Cl$_2$ (3 ml) containing triethylamine (0.95 ml) at −10° was added pyridine-SO$_3$ complex (0.4 g) in DMSO (3 ml). After 1.5 h at −10° to −5° a further portion of pyridine-SO$_3$ complex (0.3 g) was added and stirring continued for 0.5 h. The mixture was poured into water and the CH$_2$Cl$_2$ removed in vacuo. The aqueous solution was acidified to pH 6 with citric acid solution, EA (3×50 ml), washed with water, dried (MgSO$_4$) and concentrated, and the residue purified by chromatography (V) gave the title compound as an oil (0.154 g). IR (CHBr$_3$) 3490, 1740, 1703 cm$^{-1}$. TLC (K) R$_f$ 0.48.

The following compounds were prepared by a similar procedure:

(b) [1α(Z),2β,5α]-(±)-7-[5-[4-Methylthio-(phenylmethoxy)]-2-(4-morpholinyl)-3-oxocyclopentyl]-5-heptenoic acid from the product of Example 2(b). IR (CHBr$_3$) 3500, 1735, 1700 cm$^{-1}$. TLC (J) R$_f$ 0.29.

(c) [1α(Z),2β,5α]-(±)-7-[2-(4-Morpholinyl-3-oxo-5-[4-(2-phenylethyl)phenylmethoxy]cyclopentyl]-5-heptenoic acid, from the product of Example 2(c). IR (CHBr$_3$) 3590, 3500, 1735, 1700 cm$^{-1}$. TLC (J) R$_f$ 0.31. Purification by chromatography (J).

(d) [1α(Z),2β,5α]-(±)-Methyl 7-[5-[4-Methylsulphonyl(phenylmethoxy)]-2-(4-morpholinyl)-3-oxocyclopentyl]-5-heptenoate from the product of Example 3(b). IR (CHBr$_3$) 1735, 1300 cm$^{-1}$. Purification by chromatography (Q).

(e) [1α(Z),2β,5α]-(±)-Methyl 7-[5-[4-methylsulphinyl(phenylmethoxy)]-2-(4-morpholinyl)-3-oxocyclopentyl]-5-heptenoate from the product of Example 3(b). IR (CHBr$_3$) 1730, 1040 cm$^{-1}$ TLC (I) R$_f$ 0.41. Purification by chromatography (I).

(f) [1α(Z),2β,5α]-(±)-7-[2-(4-Morpholinyl)-3-oxo-5-[4-(thien-2-yl)phenylmethoxy]cyclopentyl]-5-heptenoic acid, from the product of Example 4(e), m.p. 92° IR (CHBr$_3$) 3500, 1705 cm$^{-1}$. Purification by chromatography (T).

EXAMPLE 7

(a) (1α,2β,3α,5α)-(±)-3-Hydroxy-5-[[4'-methyl (1,1'-biphenyl)-4-yl]methoxy]-2-(4-morpholinyl)cyclopentane heptanoic acid A solution of the product of Example 2(a) (0.78 g) in EA (35 ml) was hydrogenated at atmospheric pressure over pre-reduced 10% palladium oxide on charcoal (0.4 g) at 20° for 4 h. The mixture was filtered ('Hyflo') and the filtrate evaporated to give the title compound as an oil (0.75 g). IR (CHBr$_3$) 3580/3560, 3500, 1725, 1715 cm$^{-1}$. TLC (X) R$_f$ 0.4.

The following compounds were prepared by a similar procedure:

(b) (1α,2β,3α,5α)-(±)-3-Hydroxy-2-(4-morpholinyl)-5-[4-phenylmethyl)phenylmethoxy]cyclopentane heptanoic acid from the product of Example 4(b). A sample was converted into the hydrochloride salt to give material of m.p. 125°-128° (dec). IR (Nujol) 3300, 2800/2400, 1690 cm$^{-1}$.

(c) (1α,2β,3α,5α)-(±)-3-Hydroxy-5-[(4'-methoxy(1,1'-biphenyl)-4-yl]methoxy]-2-(4-morpholinyl)cyclopentane heptanoic acid, from the free base of the product of Example 4(a). IR (CHBr$_3$) 3500, 1725, 1703 cm$^{-1}$.

EXAMPLE 9

(a) [1α(Z),2β,3α,5α]-(±)-7-[5-[4-N,N-Dimethylaminosulphonyl(phenylmethoxy)]-3-hydroxy-2-(4-morpholinyl)cyclopentyl]-5-heptenoic acid A solution of Intermediate 38 (0.77 g) in methanol (30 ml) containing 2 N NaOH (5 ml) was stirred at room temperature for 18 h. The solution was treated with pH 6.5 buffer (Na$_2$HPO$_4$/KH$_2$PO$_4$) and extracted with CH$_2$Cl$_2$. The dried (MgSO$_4$) extracts were evaporated to give the title compound (0.612 g) as a foam.

IR (CHBr$_3$) 3580, 3500, 1730, 1703, 1340 cm$^{-1}$. Analysis Found: C, 58.6; H, 7.4; N, 5.1. C$_{25}$H$_{38}$N$_2$O$_7$S requires: C, 58.8; H, 7.5; N, 5.5%.

The following compounds were prepared using a similar procedure:

(b) [1α(Z),2β,3α,5α]-(±)-7-[3-Hydroxy-5-[[4'-methoxy(1,1'-biphenyl)-4-yl]methoxy]-2-(1-piperidinyl)cyclopentyl]-5-heptenoic acid, from the product of Example 1(d), m.p. 94°–101°.

Analysis Found: C, 73.0; H, 8.1; N, 2.6. C$_{31}$H$_{41}$NO$_5$ requires: C, 73.3; H, 8.1; N, 2.8%.

(c) [1α(Z),2β,3α,5α]-(±)-7-[3-Hydroxy-5-[4-(phenylmethyl)phenylmethoxy]-2-(1-piperidinyl)cyclopentyl]-5-heptenoic acid, from the product of Example 1(e), m.p. 103°–110.5°. IR (CHBr$_3$) 3500, 1730–1700(br) cm$^{-1}$.

(d) [1α(Z),2β,3α,5α]-(±)-7-[3-Hydroxy-5-[[4'-methyl(1,1'-biphenyl)-4-yl]methoxy]-2-(1-piperidinyl)cyclopentyl]-5-heptenoic acid from the product of Example 1(f), m.p. 52°–65°. TLC 3:1 Methanol-EA R$_f$0.26.

(e) [1α(Z),2β,3α,5α]-(±)-7-[3-Hydroxy-5-[[4'-methoxy(1,1'-biphenyl)-4-yl]methoxy]-2-(4-thiomorpholinyl)cyclopentyl]-5-heptenoic acid, S-dioxide from the product of Example 1 (g), IR (CHBr$_3$) 3500, 1735, 1705 cm$^{-1}$. TLC (I) R$_f$0.33.

(f) [1α(Z),2β,3α,5α]-(±)-7-[3-Hydroxy-5-[4-(phenylmethyl)phenylmethoxy]-2-(4-thiomorpholinyl)cyclopentyl]-5-heptenoic acid, S-dioxide from the product of Example 1(h), IR (CHBr$_3$) 3580, 3500, 1733, 1710 cm$^{-1}$. TLC (Q) R$_f$0.35.

(g) [1α(Z),2β,3α,5α]-(±)-7-[3-Hydroxy-5-[[4'-methyl(1,1'-biphenyl)-4-yl]methoxy]-2-(4-thiomorpholinyl)cyclopentyl]-5-heptenoic acid, S-dioxide from the product of Example 1(i), IR (CHBr$_3$) 3600(br.), 3500, 1740, 1710 cm$^{-1}$. TLC (I) R$_f$0.36.

EXAMPLE 11

(a) [1α(Z),2β,5α]-(±)-7-[5-[[4'-Methoxy(1,1'-biphenyl)-4-yl]methoxy]-2-(4-morpholinyl)-3-oxocyclopentyl]-5-heptenoic acid To a solution of the product of Example 4(a) (1.3 g) and triethylsilyl chloride (0.56 ml) in CH$_2$Cl$_2$ (8 ml) at 0° was added triethylamine (0.475 ml) and the mixture stirred at 0° for 15 min. Simultaneously, a solution of oxalyl chloride (0.68 ml) in CH$_2$Cl$_2$ (8 ml) was cooled to −70° under nitrogen and DMSO (1.35 ml) added dropwise. After stirring for 10 min. the solution of triethylsilyl ester described above was added and stirring continued at −70° for 0.75 h. Triethylamine (4 ml) was added and the cooling bath removed. When room temperature was attained the mixture was poured into NH$_4$Cl solution (100 ml) and extracted with ether (3×70 ml). The combined extracts were evaporated to leave an oily residue which was stirred with KH$_2$PO$_4$ (1 g) in acetone (5 ml), water (20 ml) and ether (5 ml) at 20° for 1.5 h. After dilution with water (100 ml) the mixture was extracted with ether (2×100 ml), dried and evaporated to give an oil (1.71 g). A portion (1.25 g) was chromatographed (J) to give an oil which crystallised from ether-isopentane at −20° to gve the title compound (0.175 g), m.p. 79°–82°, Analysis Found: C, 70.7; H, 7.2; N, 2.8. C$_{30}$H$_{37}$NO$_6$ requires: C, 71.0; H, 7.4; N, 2.8%.

The following compounds were prepared by a similar procedure:

(b) [1α(Z),2β,5α]-(±)-7-[2-(4-Morpholinyl)-3-oxo-5-[[4-(phenylmethyl)phenyl]methoxy]cyclopentyl]-5-heptenoic acid, m.p. 68°–71° (from ether-isopentane) from the free base of the product of Example 4(b).

(c) [1α(Z),2β,5α]-(±)-7-[2-(4-Morpholinyl)-3-oxo-5-[[(1,1';4.1''-terphenyl)-4-yl]methoxy]cyclopentyl]-5-heptenoic acid, m.p. 126°–128° (dec.) (from EA-PE (b.p. 60°–80°)) from the product of Example 4(c). Purification by chromatography (AB).

(d) (1α,2β,5α)-(±)-2-(4-Morpholinyl)-3-oxo-5-[4-(phenylmethyl)phenylmethoxy]cyclopentaneheptanoic acid from the product of Example 7(b), mp 83°–85°. Purification by chromatography (J) IR (Nujol) 1740, 1718 cm$^{-1}$.

(e) [1α(Z),2β,5α]-(±)-7-[5-[[4'-Methoxy(1,1'biphenyl)-4-yl]methoxy]-3-oxo-2-(1-piperidinyl)cyclopentyl]-5-heptenoic acid, from the product of Example 9(b) except that trimethylsilyl chloride and toluene were used instead of triethylsilyl chloride and CH$_2$Cl$_2$. Purification by chromatography (J) IR (Nujol) 1740, 1710 cm$^{-1}$ Analysis Found: C, 73.7; H, 8.0; N, 2.8. C$_{31}$H$_{39}$NO$_5$ requires C, 73.6; H, 7.8; N, 2.8%

(f) [1α(Z),2β,5α]-(±)-7-[3-Oxo-5-[4-(phenylmethyl)phenylmethoxy]-2-(1-piperidinyl)cyclopentyl]-5-heptenoic acid, from the product of Example 9(c). Purification by chromatography (AC). IR (Neat) 2800–2500, 1735, 1710 cm$^{-1}$. TLC (J) R$_f$0.32

(g) [1α(Z),2β,5α]-(±)-7-[5-[[4'-Methyl(1,1'-biphenyl)-4-yl]methoxy]-3-oxo-2-(1-piperidinyl)cyclopentyl]-5-heptenoic acid, from the product of Example 9(d). Purification by chromatography (J). IR (CHBr$_3$) 3500, 1735, 1700 cm$^{-1}$. TLC (J) R$_f$0,27

(h) [1α(Z),2β,5α]-(±)-7-[5-[[4'-Methoxy(1,1'-biphenyl)-4-yl]methoxy]-3-oxo-2-(4-thiomorpholinyl)cyclopentyl]-5-heptenoic acid, S-dioxide, from the product of Example 9(e). Purification by chromatography (AD) IR (CHBr$_3$) 3450, 1740, 1700 cm$^{-1}$. TLC (I) R$_f$0.38

(i) [1α(Z),2β,5α]-(±)-7-[3-Oxo-5-[4-(phenylmethyl)phenylmethoxy]-2-(4-thiomorpholinyl)cyclopentyl]-5-heptenoic acid, S-dioxide, from the product of Example 9(f) m.p. 100°–101.5°. IR (CHBr$_3$) 3490, 1745, 1710 cm$^{-1}$. Purification by chromatography (J)

(j) [1α(Z),2β,5α]-(±)-7-[5-[[4'-Methyl(1.1-Methyl(1,1'-biphenyl)-4-yl]methoxy]-3-oxo-2-(4-thiomorpholinyl)cyclopentyl]-5heptenoic acid, S-dioxide, from the product of Example 9(g) Purification by chromatography (J). IR (CHBr$_3$) 3480, 1740, 1700 cm$^{-1}$ TLC (I) R$_f$0.5

EXAMPLE 12

[1α(E),2β,3α,5α]-(±)-7-[3-Hydroxy-5-[[4'-methyl(1,1'-biphenyl)-4-yl]methoxy]-2-(4-morpholinyl)cyclopentyl]-5-heptenoic acid A solution of the product of Example 2(a) (0.28 g) and p-toluene sulphinic acid (0.133 g) in dry 1,4-dioxan (20 ml) was heated under reflux under nitrogen for 3 h. After cooling, EA (25 ml) was added, the solution washed with aqueous pH 6 phosphate buffer (30 ml), dried and concentrated. Purification by chromatography (X) EA-methanol gave the title compound as an oil (0.228 g). IR (CHBr$_3$) 3580, 3500, 1720, 1705 cm$^{-1}$.

EXAMPLE 13

[1α(Z),2β,3α,5α]-(±)-7-[5-[[4'-Chloro(1,1'-biphenyl)-4-yl]methoxy]-3-hydroxy-2-(4-morpholinyl)-cyclopentyl]-5-heptenoic acid A solution of Intermediate 40 (1.7 g) in 10% concentrated sulphuric acid in methanol (30 ml) was stirred for 16 h. The solution was neutralised with 8% NaHCO$_3$ solution and extracted into CH$_2$Cl$_2$. The extracts were evaporated and the residue then dissolved in a solution of KOH (0.4 g) in methanol (20 ml) and water (10 ml). After 24 h at room temperature, the solution was treated with NaHSO$_4$ solution until pH 6.5, whereupon the mixture was extracted with CH$_2$Cl$_2$. The dried (MgSO$_4$) extracts were concentrated and the residue purified by chromatography (AG) followed by (AH) to give the title compound as a foam (0.45 g). IR (CHBr$_3$) 3600-3440, 1730, 1700 cm$^{-1}$. TLC 9:1 Chloroform-methanol R$_f$ 0.7.

EXAMPLE 15

[1α(Z),2β,3α,5α]-(±)-Methyl 7-[5-[4-Acetylamino(phenylmethoxy)]-3-hydroxy-2-(4-morpholinyl)cyclopentyl]-5-heptenoate Anhydrous K$_2$CO$_3$ (0.21 g) was added to a stirred solution of Intermediate 35 (0.61 g) in dry methanol (20 ml). After 2.5 h, the suspension was poured into saturated NH$_4$Cl solution (50 ml), extracted with CH$_2$Cl$_2$ (3×30 ml), dried (MgSO$_4$), filtered and evaporated, and the residue purified by column chromatography (AJ) to give the title compound as an oil (0.5 g). IR (CHBr$_3$) 3500 (br), 3420, 1725, 1685, 1510 cm$^{-1}$. TLC (AJ) Rf 0.38

EXAMPLE 16

[1α(Z),2β,5α]-(±)-Methyl 7-[5-[4-Acetylamino(phenylmethoxy)]-2-(4-morpholinyl)-3-oxocyclopentyl]-5-heptenoate Pyridinium trifluoroacetate (0.21 g) was added to a stirred mixture of the product of Example 15 (0.35 g) and dicyclohexylcarbodiimide (0.61 g) in dry DMSO (6 ml). After 30 min. the suspension was poured into water (50 ml), extracted with ether (3×40 ml), dried (MgSO$_4$), filtered and evaporated to afford an oil, which was purified by colum chromatography (AK) to give the title compound as a solid (0.3 g) m.p. 88°-88.5°.

EXAMPLE 17

(a) [1α(Z),2β,5α]-(±)-Methyl 7-[5-[4-Methylthio(phenylmethoxy)]-2-(4-morpholinyl)-3-oxocyclopentyl]-5-heptenoate A solution of the product of Example 5(b) (0.5 g) in ether (10 ml) was treated with an excess of ethereal CH$_2$N$_2$ at room temperature. Excess CH$_2$N$_2$ was destroyed by the addition of acetic acid. The solution was diluted with water and washed with 8% NaHCO$_3$ solution followed by water. Evaporation of the dried solvent afforded an oil which was purified by chromatography (G) to give the title compound (0.3 g) IR (CHBr$_3$) 1735 cm$^{-1}$.

The following compounds were prepared by a similar procedure:

(b) [1α(Z),2β,5α]-(±)-Methyl 7-[5-[[4'-Methyl(1,1'-biphenyl)-4-yl]methoxy]-2-(4-morpholinyl)-3-oxocyclopentyl]-5-heptenoate, m.p. 82°-86° (from ether-PE (b.p. 60°-80°)) from the product of Example 5(a), (c) [1α(Z),2β,5α]-(±)-Methyl 7-[5-[[4'-Methoxy(1,1'-biphenyl)-4-yl]methoxy]-2-(4-morpholinyl)-3-oxocyclopentyl]-5-heptenoate, m.p. 79°-84° (from EA-PE (b.p. 60°-80°)) from the product of Example 11(a).

(d) [1α(Z),2β,5α]-(±)-Methyl 7-[2-(4-Morpholinyl-3-oxo-5-[[[4-(phenylmethyl)phenyl]-4-yl]methoxy]cyclopentyl]-5-heptenoate, m.p. 30°-33° (from ether-isopentane at −20° from the product of Example 11(b).

EXAMPLE 18

(a) (1α,2β,5α)-(±)-5-[[4'-Methyl(1,1'-biphenyl)-4-yl]methoxy]-2-(4-morpholinyl)-3-oxocyclopentaneheptanoic acid A stirred solution of the product of Example 7(a) (0.695 g) in acetone (20 ml) was cooled to −10° and Jones reagent (2.67 M, 0.75 ml) added dropwise. After 1.25 h at −10° to −5° a further aliquot of Jones reagent (0.15 ml) was added and stirring continued for a further 0.5 h, whereupon the mixture was poured into pH 6.5 phosphate buffer (100 ml) and extracted with CH$_2$Cl$_2$ (3×30 ml), dried (MgSO$_4$), filtered and evaporated, and the residue purified by chromatography (J) followed by (AL) to give the title compound which crystallised from ether-EA-PE (b.p. 60°-80°) as needles (0.345 g), m.p. 88°-89°.

Analysis found: C, 72.5; H, 7.7; N, 2.6. C$_{30}$H$_{39}$NO$_5$ requires: C, 73.0; H, 8.0; N, 2.8%.

The following compounds were prepared using a similar procedure:

(b) [1α(Z),2β,5α]-(±)-7-[2-(4-Morpholinyl)-3-oxo-5-[4-phenylsulphonyl(phenylmethoxy)]cyclopentyl]-5-heptenoic acid, from the product of Example 4(d). Purification by chromatography (J) IR (CHBr$_3$) 3490, 1730, 1730, 1700, 1070 cm$^{-1}$. TLC (J) R$_f$ 0.16.

(c) [1α(E),2β,5α]-(±)-7-[5-[[4'-Methyl(1,1'-biphenyl)-4-yl]methoxy]-2-(4-morpholinyl)-3-oxocyclopentyl]-5-heptenoic acid, from the product of Example 12. Purification by chromatography (J). m.p. 82°-93°.

Analysis found: C, 73.0; H, 7.6; N, 2.6. C$_{30}$H$_{37}$NO$_5$ requires: C, 73.3; H, 7.6; N, 2.9%.

(d) (1α,2β,5α)-(±)-5-[[4'-Methoxy(1,1'-biphenyl)-4-yl]-2-(4-morpholinyl)-3-oxocyclopentane]heptanoic acid, from the product of Example 7(c) m.p. 87°-90°.

Analysis found: C, 70.7; H, 8.1; N, 3.0. C$_{30}$H$_{39}$NO$_6$ requires: C, 70.7; H, 7.7; N, 2.8%.

(e) [1α,(Z),2β,5α]-(±)-7-[5-[4-N,N-Dimethylaminosulphonyl(phenylmethoxy)]-2-(4-morpholinyl)-3-oxocyclopentyl]-5-heptenoic acid, from the product of Example 9(a). Purification by chromatography (AL). IR (CHBr$_3$) 3480, 1738, 1700, 1340 cm$^{-1}$.

Analysis found: C, 58.9; H, 7.1; N, 5.3. C$_{25}$H$_{36}$N$_2$O$_7$S requires: C, 59.0; H, 7.1; N, 5.5%.

(f) [1α(Z),2β,5α]-(±)-7-[5-[[4'-Chloro(1,1'-biphenyl)-4-yl]methoxy]-2-(4-morpholinyl)-3-oxocyclopentyl]-5-heptenoic acid, from the product of Example 13. Purification by chromatography (AG) followed by (T). IR (CHBr$_3$) 3500, 1740, 1700 cm$^{-1}$. TLC 95:5 chloroform-methanol R$_f$ 0.4.

PHARMACEUTICAL EXAMPLES

| Tablets Direct Compression | Mg/tablet |
|---|---|
| Active ingredient | 100.00 |

-continued

| Tablets Direct Compression | Mg/tablet |
|---|---|
| Microcrystalline Cellulose B.P.C. | 298.00 |
| Magnesium Stearate | 2.00 |
| Compression Weight | 400.00 |

The active ingredient is sieved through a 250 m$^{-6}$ sieve, blended with the excipients and compressed using 10.0 mm punches. Tablets of other strengths may be prepared by altering the compression weight and using punches to suit.

| Injection for Intravenous Administration | %w/v |
|---|---|
| Active ingredient | 0.50 |
| Water for injections B.P. to | 100.00 |

Sodiun chloride may be added to adjust the tonicity of the solution and the pH may be adjusted to that of maximum stability and/or to facilitate solution of the active ingredient using either dilute acid or alkali.

The solution is prepared clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

| Inhalation Cartridges | /cartridge |
|---|---|
| Active ingredient (micronised) | 3 mg |
| Lactose B.P. to | 25 mg |

The active ingredient is micronised so that the majority of the particles are between 1 m$^{-6}$ and 5 m$^{-6}$ in longest dimension and none are greater than 10 m$^{-6}$. The active ingredient is then blended with the lactose and the mix is filled into No. 3 hard gelatin capsules using a suitable filling machine.

British Patent Specification No. 2,028,805A referred to above corresponds to U.S. patent application 056,416 (Collington et al) which is incorporated herein by reference.

We claim:

1. A compound of the formula

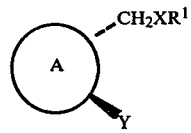

in which
A represents

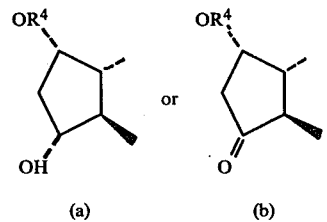

(a)      (b)

X is cis or trans —CH═CH— or —(CH$_2$)$_2$—;

R$^1$ is straight or branched C$_{1-7}$ alkyl bearing as a terminal substituent —COOR$^{10}$ where R is a hydrogen atom, C$_{1-6}$ alkyl or C$_{7-10}$ aralkyl;

Y is a saturated heterocyclic amino group which has 5–8 ring members, and optionally contains in the ring one or more —O—, —S—, —SO$_2$—, —NR$^{14}$—, or ⟩C(OH)R$^6$ substituents; wherein R$^{14}$ is a hydrogen atom, C$_{1-7}$ alkyl or aralkyl having a C$_{1-4}$ alkyl portion, R$^6$ is a hydrogen atom, C$_{1-7}$ alkyl, phenyl or aralkyl having a C$_{1-4}$ alkyl portion; and said saturated heterocyclic amino group is optionally substituted by one or more C$_{1-4}$ alkyl groups;

R$^4$ is a phenalkyl group having a C$_{1-3}$ alkyl portion and a phenyl portion substituted with C$_{1-3}$ alkylthio, C$_{1-3}$ alkylsulphinyl, C$_{1-3}$ alkylsulphonyl, C$_{1-3}$ alkanoylamino, benzoylamino, phenylalkyl having a C$_{1-3}$ alkyl portion, aminosulphonyl having the amino group optionally substituted by one or more C$_{1-3}$ alkyl groups, C$_{1-3}$ alkanoylaminosulphonyl having the amino group optionally substituted by C$_{1-3}$ alkyl, phenylsulphony having the phenyl portion optionally substituted by C$_{1-3}$ alkyl, nitro, tetrazol-5-yl, thienyl, or phenyl substituted by R$^5$ where R$^5$ is C$_{1-4}$ alkyl, C$_{1-4}$ alkoxy, halogen or phenyl;

and the physiologically acceptable salts thereof.

2. A compound as claimed in claim 1 in which A is the group (b).

3. A compound of the claim 1 wherein Y is a saturated heterocyclic amino group selected from the group consisting of pyrrolidino, piperidino, piperidino substituted by hydroxy, morpholino, piperazino, thiamorpholino, 1-dioxothiamorpholino, homomorpholino, or hexamethyleneimino.

4. A compound as claimed in claim 1, 2 or 3 in which X is cis —CH═CH—.

5. A compound as claimed in claim 1, 2 or 3 in which R$^1$ is —(CH$_2$)$_3$COOR$^{10}$ where R$^{10}$ is a hydrogen atom or C$_{1-4}$ alkyl.

6. A compound as claimed in claim 1, 2 or 3 in which R$^4$ is benzyl substituted by phenyl-(C$_{1-3}$) alkyl, or phenyl substituted by C$_{1-3}$ alkoxy or C$_{1-3}$ alkyl.

7. A compound as claimed in claim 1, in which:
A is the group (b),
X is cis —CH═CH—,
R$^1$ is —(CH$_2$)$_3$COOH,
Y is morpholino, piperidino or dioxothiamorpholino, and
R$^4$ is benzyl substituted by phenethyl, benzyl, methoxyphenyl or methylphenyl.

8. A composition comprising a compound as claimed in claim 1, 2, 3 or 7 with one or more pharmaceutical carriers.

* * * * *